United States Patent [19]

Cohen

[11] 4,150,050

[45] Apr. 17, 1979

[54] 3,6-DIOXO-1,4-CYCLOHEXADIEN-1-YL-BUTANDATE ESTERS

[75] Inventor: Noal Cohen, Montclair, N.J.

[73] Assignee: Hoffmann-La Roche Inc., Nutley, N.J.

[21] Appl. No.: 873,185

[22] Filed: Jan. 30, 1978

[51] Int. Cl.² ............................................ C07C 143/68
[52] U.S. Cl. .............................. 260/456 R; 260/345.5; 560/126
[58] Field of Search .................................. 260/456 R

[56] References Cited

U.S. PATENT DOCUMENTS 3,947,473   3/1976   Scott et al. ...................... 260/345.5

*Primary Examiner*—Nicky Chan
*Attorney, Agent, or Firm*—Jon S. Saxe; Bernard S. Leon; William H. Epstein

[57] ABSTRACT

A process for inversion of the stereo configuration of (R)-(+)-3,4-dihydro-6-hydroxy-2,5,7,8-tetraalkyl-2H-1-benzopyran-2-carboxylic acid and derivatives thereof to form the corresponding S-(−) acid and intermediates in this process.

2 Claims, No Drawings

3,6-DIOXO-1,4-CYCLOHEXADIEN-1-YL-BUTAN-DATE ESTERS

BACKGROUND OF INVENTION

U.S. Pat. No. 3,947,473, Scott et al., discloses a compound

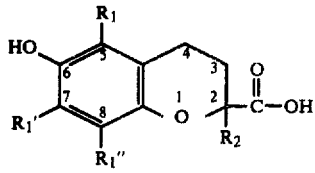

I wherein $R_1$, $R_1'$, and $R_1''$ are independently hydrogen or lower alkyl, and $R_2$ is lower alkyl
and a method for resolving this compound into its two isomeric forms, i.e.

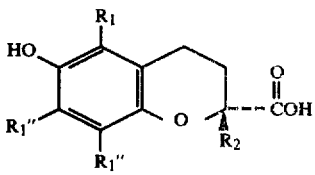

I-A and

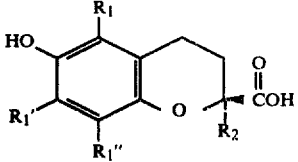

I-B wherein $R_1$, $R_1'$, $R_1''$ are $R_2$ are as above.

In many cases, it is desired to utilize the compound of formula I in its 2S form, i.e. the compound of formula I-B. This is especially true where $R_1$, $R_1'$, $R_1''$ and $R_2$ are methyl since this compound is an intermediate for natural optically active alpha-tocopherol, i.e. alpha tocopherol having the 2R,4'R and 8'R configuration. Therefore, the compound of formula I-A may be the undesired isomer and the conversion to the optically pure 2S form be desired.

SUMMARY OF INVENTION

In accordance with this invention, it has been discovered that the optically pure 2R compounds of formula I-A can be inverted to form the optically pure 2S-isomer. Therefore, this invention provides a method for utilizing the unwanted 2R-isomer for producing(2R,4'R,8'R)alpha-tocopherol. In this manner, both the isomers of formula I can be used, thereby improving the economy of the overall synthesis of (2R,4'R,8'R)-α-tocopherol (natural Vitamin E). Further, it provides a method for forming the antioxidants of formula I in their optically active 2S-configuration with an improved economy.

DETAILED DESCRIPTION

In the structural formula given throughout this application, the substituents attached to the molecule above the plane of the molecule are designated by ◄ and the substituents attached to the molecule below the plane of the molecule are designated by ▏ . The numbering of the chromane ring in the compound of formula I is given for the purpose of convenience.

As used herein, the term lower alkyl designates straight and branched chain aliphatic saturated hydrocarbon groups containing from 1 to 7 carbon atoms such as methyl, ethyl, n-propyl, isopropyl, tert-butyl, isobutyl, etc. The term halogen includes all four halogens, i.e. chlorine, bromine, fluorine and iodine.

The compounds of formula I-A are converted to the compound of formula I-B via the following intermediates:

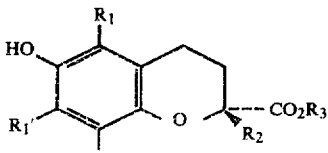

II

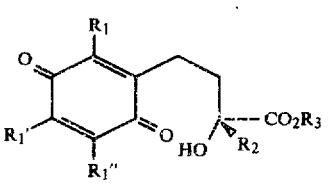

III

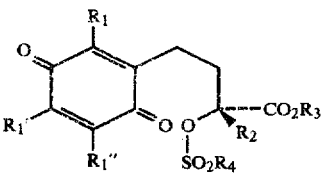

IV

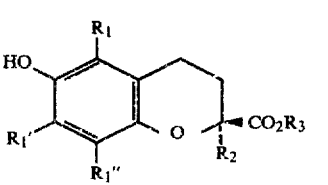

V wherein $R_1$, $R_1'$, $R_1''$ and $R_2$ are as above, and $R_3$ is lower alkyl, and $R_4$ is lower alkyl.

In accordance with this invention, the compound of formula I-A is inverted to the compound of formula I-B in a simple and economical manner. By the process of this invention, the compound of formula I-A can be directly converted to the compound of formula I-B in a simple and economic manner.

The first step of this invention is carried out by esterifying the compound of formula I-A with a lower alkanol to form the compound of formula II. Any conventional method of esterifying an organic acid with a lower alkanol can be utilized to carry out this reaction. Among the preferred methods for esterification is reacting the compound formula I-A with a lower alkanol such as methanol in the presence of an organic acid such as p-toluene sulfonic acid. Generally, the lower alkanol can act as the solvent medium.

The compound of formula II is converted to the compound of formula III by treating the compound of formula II with an oxidizing agent. Any conventional oxidizing agents can be utilized to carry out this reaction. The oxidizing agents which are utilized can be any conventional oxidizing agent which converts hydroquinone to benzoquinones. Among the preferred oxidizing agents are included Ferric chloride, nitric acids, ceric sulfate, etc. Any of the conditions conventional in utilizing these oxidizing agents can be utilized in carrying out this reaction.

The compound of formula III is converted to the compound of formula IV by treatment with a compound of the formula:

$$R_4SO_2X \qquad \qquad VIII$$

wherein $R_4$ is as above; and
X is halogen.

In the compound of formula VIII, $R_4$ can be any lower alkyl group. The preferred compound of formula VIII is methane sulfonyl chloride.

Generally the reaction of the compound of formula III with the compound of formula VIII to produce a compound of the formula IV is carried out in the presence of an organic amine base. Any conventional organic amine base can be utilized in carrying out this reaction. Among the preferred bases are included the tri(lower alkyl)amines and pyridine. Any conventional tri(lower alkyl)amine can be utilized in carrying out this reaction. Among the preferred amines are included methyl-diethyl amine, triethyl amine, trimethyl amine, etc. Generally, this reaction is carried out in the presence of an inert organic solvent. Any conventional inert organic solvent can be utilized. Among the preferred inert organic solvents are the halogenated hydrocarbons such as dichloromethane. In carrying out this reaction, temperatures from −20° C. to +10° C. are generally utilized.

The compound of formula IV is converted to the compound of formula V by treating the compound of formula IV with a reducing agent and a base. In accordance with this invention, it has been discovered that this process occurs with complete inversion of stereo configuration. This reaction can be carried out by treating the compound of formula IV with a reducing agent in the presence of a base. The reducing agent can be any conventional quinone reducing agent. Any of the conventional reducing agents utilized to reduce quinones to hydroquinones can be utilized in carrying out the process of this invention. Among the preferred quinone reducing agents are included alkali metal hydrosulfites, alkalimetal borohydrides, or catalytic hydrogenation. Where an alkali metal borohydride is utilized, the preferred borohydrides are sodium borohydride, potassium borohydride, and lithium borohydride. The preferred alkali metal hydrosulfites, are sodium and potassium hydrosulfites. Among the preferred catalysts for use in catalytic hydrogenation are palladium and platinum as well as the other metals which are conventionally used in catalytic hydrogenation. These catalysts can be used alone or on conventional supports such as charcoal or carbon.

Any conventional base may be present in this reaction during the treatment of the compound of formula IV with a reducing agent. On the other hand, the base can be utilized after the reduction has been carried out. Any conventional base can be utilized in carrying out this reaction. Among the preferred bases are the inorganic bases such as the alkali metal hydroxides as well as the organic bases such as the alkali metal lower alkoxides, pyridine and the (lower alkyl)amines mentioned hereinbefore.

Generally, this reaction is carried out in a polar solvent. Among the conventional polar solvents are included lower alkanols, ethers such as diethyl ether or tetrahydrofuran. Any conventional polar solvent can be utilized in carrying out this reaction. In carrying out this reaction, temperature and pressure are not critical and this reaction can be carried out at room temperature and atmospheric pressure. On the other hand, elevated or reduced temperatures can be utilized. Generally, it is preferred to carry out this reaction in a temperature of from 0° C. to 70° C.

The compound of formula V is converted to the compound of formula I-B by hydrolysis. Any conventional method of ester hydrolysis can be utilized to carry out this conversion.

The following examples are illustrative but not limitative of the claimed invention. In the Examples, the ether is diethyl ether. In the following examples, the "usual work-up" involves 3 extractions with the specified solvent. The organic extracts were then washed with water and saturated brine, dried over anhydrous magnesium sulfate, filtered and concentrated at 40°–50° C. under water aspirator pressure. Residues were dried to constant weight under high vacuum. Unless otherwise noted, reactions were carried out under an atmosphere of argon. Column chromatography was performed using silica gel.

EXAMPLE 1

(R)-(+)-3,4-Dihydro-6-hydroxy-2,5,7,8-tetramethyl-2H-1-benzopyran-2-carboxylic Acid Methyl Ester A solution of 2g(8 mmoles) of optically pure (R)-(+)-3,4-dihydro-6-hydroxy-2,5,7,8-tetramethyl-2H-1-benzopyran-2-carboxylic acid; $[\alpha]_D^{25}$ + 65.84° (c 1.18, $C_2H_5OH$) and 0.1g of p-toluenesulfonic acid monohydrate in 40 ml of methanol was stirred and refluxed for 3.75 hr. After cooling, the solution was diluted with water and worked-up with ether in the usual manner (the ether extracts were additionally washed with saturated aqueous sodium bicarbonate solution) giving 2g (94.7%) of (R)-(+)-3,4-dihydro-6-hydroxy-2,5,7,8-tetramethyl-2H-1-benzopyran-2-carboxylic acid methyl ester as a colorless solid, mp 132°–134.5°; $[\alpha]_D^{25}$ + 61.4° (c 4.91, $CH_3OH$). The analytical specimen was obtained by recrystallization of a sample from aqueous methanol as a colorless solid, mp 133.5°–135°; $[\alpha]_D^{25}$ + 61.85° (c 5.07, $CH_3OH$).

EXAMPLE 2

(R)-(−)-Methyl 2-Hydroxy-2-methyl-4-(2,4,5-trimethyl-3,6-dioxo-1,4-cyclohexadien-1-yl) butanoate To a stirred solution of 1.5g (5.68 mmoles) of (R)-(+)-3,4-dihydro-6-hydroxy-2,5,7,8-tetramethyl-2H-1-benzopyran-2-carboxylic acid methyl ester in 22 ml of ether, was added a solution of 4.5g (16.6 mmoles) of ferric chloride hexahydrate in 17 ml of water and 17 ml of methanol. The addition was carried out in approximately 6 ml portions at 0.5 hr intervals. One-half hour after the last addition, the ether layer was separated and the aqueous phase was further worked-up by ether extraction in the usual manner. There was obtained 1.5g of a yellow oil which was chromatographed on 75g of silica gel. Elution with 9:1 parts by volume and 4:1 parts by volume toluene-ethyl acetate yielded 1.35g (84.9%) of (R)-(+)-methyl 2-hydroxy-2-methyl-4-(2,4,5-trimethyl-3,6-dioxo-1,4-cyclohexadien-1-yl) butanoate as a yellow oil; $[\alpha]_D^{25}$ −21.01° (C 0.96, $CHCl_3$).

EXAMPLE 3

A suspension of 2.64g (10 mmoles) of (R)-(+)-3,4-dihydro-6-hydroxy-2,5,7,8-tetramethyl-2H-1-benzopyran-2-carboxylic acid methyl ester ($[\alpha]_D^{25}$ + 61.00° ( c 3.05, CH$_3$OH) in 25 ml of ether was vigorously stirred with ice-bath cooling while 5 ml (80 mmoles) of 70% by weight aqueous nitric acid was added dropwise over a 15 min period. The resulting bright yellow solution was cautiously poured into excess saturated aqueous sodium bicarbonate solution. Work-up with ether in the usual manner gave 2,78g (99.5%) of (R)-(−)-methyl 2-hydroxy-2-methyl-4-(2,4,5-trimethyl-3,6-dioxo-1,4-cyclohexadien-1-yl) butanoate as a yellow oil. This material was identical with that produced as in Example 2 above.

EXAMPLE 4

(R)-(−)-Methyl 2-Methyl-2-[(methylsulfonyl)oxyl-4-(2,4,5-trimethyl-3,6-dioxo-1,4-cyclohexadien-1-yl)butanoate To a stirred solution of 0.74g (2.66 mmoles) (R)-(−)-methyl 2-hydroxy-2-methyl-4-(2,4,5-trimethyl-3,6-dioxo-1,4-cyclohexadien-1-yl)butanoate in 18 ml of dichloromethane, cooled in an ice-bath, was added 2.43 ml (1.77g; 17.5 mmoles) of triethylamine followed by 1.35 ml (2.01g; 17.5 mmoles) of methanesulphonyl chloride. The mixture was kept at 0° for 64 hr then treated with water. The dichloromethane solution was processed in the usual manner to give 1.45g of an oily product which was chormatographed on 75g of silica gel. Elution with 9:1 parts by volume toluene-ethyl acetate afforded 0.69g (72.5%) of (R)-(−)-methyl 2-methyl-2-[(methylsulfonyl)oxy]-4-(2,4,5-trimethyl-3,6-dioxo-1,4- cyclohexadien-1-yl)butanoate as a yellow solid. Recrystallization of a sample from hexane-ethyl acetate provided yellow crystals, mp 112°-114°; $[\alpha]_D^{25}$ −5.24° (c 1.05, CHCl$_3$).

EXAMPLE 5

(S)-(+)-3,4-Dihydro-6-hydroxy-2,5,7,8-tetramethyl-2H-1-benzopyran-2-carboxylic Acid Methyl Ester A slurry of 0.358g (1 mmole) of (R)-(−)-methyl-2-[(methylsulfonyloxy]-4-(2,4,5-trimethyl-3,6-dioxo-1,4-cyclohexadien-1-yl)butanoate in 5 ml of methanol was stirred rapidly, at room temperature, while a solution of 0.261g (1.5 mmoles) of sodium dithionite in 3 ml of 1N aqueous sodium hydroxide was added dropwise over a 5 min period. The resulting mixture was stirred at room temperature for 20 min then refluxed for 5 min. After cooling, 20 ml of water was added and the colorless slurry was filtered with suction. The solid was washed with water then dried under high vacuum giving 0.246g (93.2%) of (S)-(−)-3,4-dihydro-6-hydroxy-2,5,7,8-tetramethyl-2H-1-benzopyran-2-carboxylic acid methyl ester as a colorless solid, mp 132.5°-135°; $[\alpha]_D^{25}$ −60.62° (c 3.09, CH$_3$OH). This material was homogeneous on TLC analysis.

EXAMPLE 6

A mixture of 1g (2.79mmoles) of (R)-(−)-methyl 2-methyl-2-[(methylsulfonyl)oxyl-4-(2,4,5-trimethyl-3,6-dioxo-1,4-cyclohexadien-1-yl)butanoate, 0.2g of 5% palladium on charcoal and 125 ml of methanol was stirred in an atmosphere of hydrogen until gas uptake ceased. The catalyst was filtered with suction on a pad of Celite and the filtrate was immediately treated with 8.3 ml (11.16 mmoles) of 1.34 M methanolic sodium methoxide. After stirring for 1 hr at room temperature, the solution was acidified with 3 N aqueous hydrochloric acid and poured into saturated brine. Work-up with ether in the usual manner gave 0.638g of a tan solid which was chromatographed on 25g of silica gel. Elution with 19:1 parts by volume and 9:1 parts by volume toluene-ethyl acetate furnished 0.491g (66.7%) of (S)-(−)-3,4-dihydro-6-hydroxy-2,5,6,8-tetramethyl-2H-1-benzopyran-2-carboxylic acid methyl ester as a colorless solid; $[\alpha]_D^{25}$ −59.93° (c 3.01, CH$_3$OH).

EXAMPLE 7

To a solution of 0.5g (1.4 mmoles) of (R)-(−)-methyl 2-methyl-2-[(methylsulfonyl)oxy]-4-(2,4,5-trimethyl-3,6-dioxo-1,4-cyclohexadien-1-yl)butanoate in 30 ml of methanol, at room temperature, was added a solution of 20.2 mg (0.53 mmole) of sodium borohydride in 10 ml of methanol, dropwise, with stirring. After stirring at room temperature for 50 min, 5.77 ml (7.73 mmoles) of 1.34 M methanolic sodium methoxide was added and stirring was continued for 2 hr, at room temperature. The resulting solution was acidifed with 1 N aqueous hydrochloric acid then poured into saturated brine and worked-up with ether in the usual manner. The crude, crystalline product (0.34g) was chromatographed on 20g of silica gel. Elution with 19:1 parts by volume toluene-ethyl acetate gave 0.311g (84.1%) of (S)-(+)-3,4-dihydro-6-hydroxy-2,5,7,8-tetramethyl-2H-1-benzopyran-2-carboxylic acid methyl ester as a colorless solid, mp 131-134°; $[\alpha]_D^{25}$ −60.46° ( c 3.88, CH$_3$OH).

I claim:

1. A compound of the formula

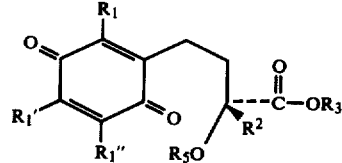

wherein R$_1$, R$_1'$ and R$_1''$ are hydrogen or lower alkyl, R$_5$ is —SO$_2$R$_6$; R$_6$ is lower alkyl and R$_2$ and R$_3$ are lower alkyl.

2. The compound of claim 1 where said compound is (R)-(+)-methyl 2-methyl-2-[(methylsulfonyl)oxy]-4-(2,4,5-trimethyl-3,6-dioxo-1,4-cyclohexadien-1-yl)butanoate.

* * * * *